(12) United States Patent
Schmotzer

(10) Patent No.: US 6,383,228 B1
(45) Date of Patent: May 7, 2002

(54) FEMORAL HIP-JOINT PROSTHESIS WITH A LOGARITHMICALLY EXTENDING CURVATURE

(75) Inventor: Hans F. Schmotzer, Kölliken (CH)

(73) Assignee: Plus Endoprothetik AG, Rotkreuz (CH)

( * ) Notice: Subject to any disclaimer, the term of this patent is extended or adjusted under 35 U.S.C. 154(b) by 0 days.

(21) Appl. No.: 09/381,852

(22) PCT Filed: Dec. 30, 1998

(86) PCT No.: PCT/CH98/00564

§ 371 Date: Oct. 14, 1999

§ 102(e) Date: Oct. 14, 1999

(87) PCT Pub. No.: WO99/40872

PCT Pub. Date: Aug. 19, 1999

(30) Foreign Application Priority Data

Feb. 11, 1998 (EP) .............................. 98102320

(51) Int. Cl.[7] .................................. A61F 2/36
(52) U.S. Cl. .................................. 623/23.35; 623/23.15
(58) Field of Search .................. 623/23.15–23.2, 623/23.22–23.31, 23.44–23.57, 23.35

(56) References Cited

U.S. PATENT DOCUMENTS

| 4,865,608 A | * | 9/1989 | Brooker, Jr. ................. 623/23 |
| 5,080,680 A | * | 1/1992 | Mikhail et al. ............... 623/23 |
| 5,156,627 A | | 10/1992 | Amstutz et al. |
| 5,593,452 A | | 1/1997 | Higham et al. |

FOREIGN PATENT DOCUMENTS

| EP | B1-0 530 323 | 3/1993 |
| EP | A1-0 554 987 | 8/1993 |
| EP | 0 790 045 A1 | 8/1997 |
| WO | WO 91/18561 | 12/1991 |

* cited by examiner

Primary Examiner—David J. Isabella
Assistant Examiner—Urmi Chattopadhyay
(74) Attorney, Agent, or Firm—Oliff & Berridge PLC

(57) ABSTRACT

A femoral hip-joint prosthesis having a tapered stem for implantation by cement. The prosthesis has a collarless shoulder at a proximal end and a stem extending therefrom to a distal end in tapered fashion. A logarithmically extending curvature of anterior and posterior side faces of a first subsidiary section of the stem combine with straight converging lines of a second subsidiary section of the stem to uniformly distribute pressure in the prosthesis within the femoral hip bone.

10 Claims, 5 Drawing Sheets

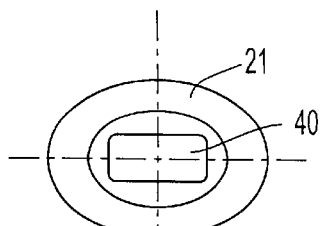
FIG. 6(b) (I-I)
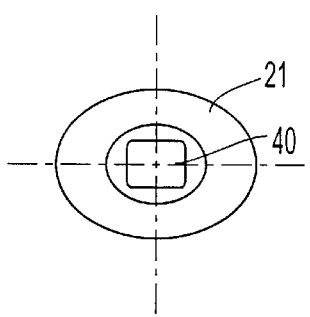
FIG. 6(c) (II-II)
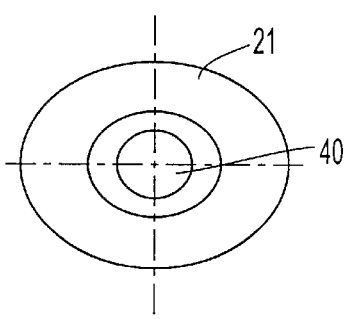
FIG. 6(d) (III-III)
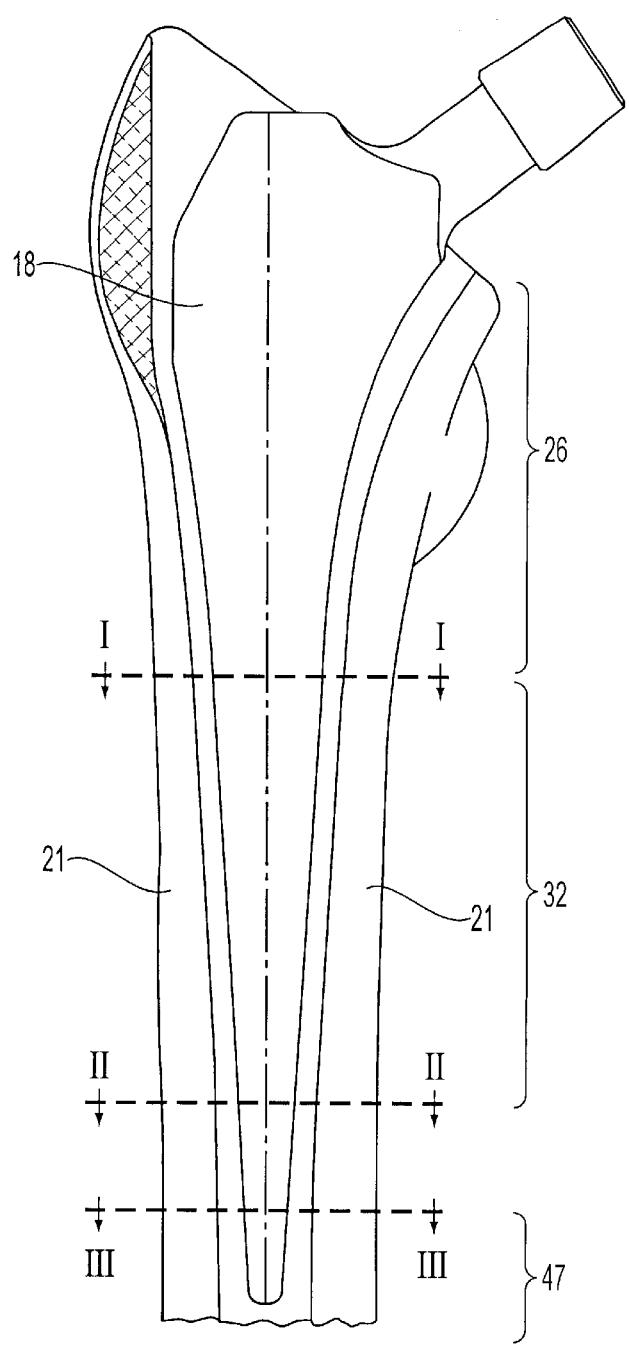
FIG. 6(a)

FEMORAL HIP-JOINT PROSTHESIS WITH A LOGARITHMICALLY EXTENDING CURVATURE

BACKGROUND OF THE INVENTION

1. Field of Invention

The invention relates to a femoral hip-joint prosthesis having a tapered stem, for implantation by cement.

2. Description of Related Art

Laid-open patent application WO 91/18561 A1 discloses a femoral hip-joint prosthesis which is designed as a wedge-shaped intramedullary stem with a collarless shoulder. In order to secure a stem of this kind in the canal of a femur, a type of bone cement is used which normally comprises a mixture of polymethyl methacrylate (hereinafter PMMA) polymer and methyl methacrylate monomer, and optionally contains a styrene copolymer of PMMA. These and other types of cement used for the purpose of securing the stem in the canal of the femoral bone are subject to a phenomenon known as creeping. Although the bone cement in the hardened state appears to be rigid, it is subject to tiny movements over the course of time, and these lead to disturbance of the microscopic denticulations constituting the cement/implant interface and the cement/bone interface. This effect can cause the stem to loosen with time. The known stem is designed in such a way that there is slight adhesion between the bone cement and the surface of the stem. If creeping of bone cement occurs, then the wedge-shaped stem easily sinks in the bone cement and automatically settles again within the bone cement. In order to prevent loosening of the stem, it is crucially important that as far as possible the creeping of the cement and sinking of the stem do not disturb the microscopic denticulations of the cement/bone interface.

A disadvantage of the known stem is the fact that because of the sinking of the stem in the femur, the pressure force exerted on the bone cement increases, particularly at the cement/implant interface, but also at the cement/bone interface, and in this case excess creeping or fissuring of the bone cement occurs in particular at those points where there is a great increase in pressure force.

SUMMARY OF THE INVENTION

The object of the present invention is to develop a femoral hip-joint prosthesis for implantation by cement in such a way that the bone cement is exposed to less stress, and in particular in such a way that there is minimal disturbance of the microscopic denticulations at the cement/bone interface.

This object is achieved with a femoral hip-joint prosthesis having a tapered stem for implantation by cement as described herein. Further advantageous embodiments of the invention are also described herein using the tapered stem femoral hip-prosthesis for implantation by cement having a logarithmically extending curvature in a first subsidiary section and a converging straight line in a second subsidiary section.

The invention is achieved in particular with a femoral hip-joint prosthesis for implantation by cement, having a collarless shoulder at the proximal end and having a stem which extends in a straight line from the shoulder to the distal end and tapers from the proximal end toward the distal end, the stem having a quadrilateral cross section and an anterior side face and a posterior side face, and the two side faces, in the direction of extension of the stem, having, in a first subsidiary section beginning at the shoulder, a logarithmically extending curvature, and the two side faces thereafter, in a second subsidiary section, extending in a straight line and converging.

The femoral hip-joint prosthesis according to the invention, hereinafter also referred to as a femoral stem, has an anterior side face and a posterior side face which, in the longitudinal direction, in a first subsidiary section beginning at the shoulder, each have a logarithmically extending curvature so that the cross section of the stem tapers toward the distal end. The anterior side face and the posterior side face each have, following the first subsidiary section, a second subsidiary section, which second subsidiary sections extend in a straight. line and converge toward the distal end.

The femoral stem according to the invention has the advantage that its configuration in the longitudinal direction corresponds approximately to the anatomical course of the medullary canal of the femur which has a trumpet-shaped structure in a first, upper subsidiary section, whereas the medullary canal, in a second, lower subsidiary section, has side walls which extend in straight lines, slightly narrowing in the distal direction. In a preferred embodiment, the femoral stem has a configuration which is adapted to the anatomical course of the medullary canal in such a way that the bone cement coming to lie between the stem and the femur has an approximately constant layer thickness. On account of the logarithmically extending curvature, the femoral stem according to the invention additionally has such a configuration that upon sinking of the femoral stem, the cement, particularly in the first, upper subsidiary section, experiences as uniform as possible a compression, which in the first subsidiary section effects an approximately uniform increase in force oriented perpendicular to the direction of extension of the femoral stem, so that stress peaks or fissures in the bone cement are avoided.

The advantage of this logarithmically extending configuration can of course also be exploited, in the first subsidiary section, by means of correspondingly logarithmically curved lateral and medial sides of the femoral hip-joint prosthesis.

A further advantage of the design of the femoral hip-joint prosthesis according to the invention lies in the fact that by avoiding stress peaks in the bone cement, the cement/bone interface has a fairly uniform distributed pressure load. It is known that in the case of a cement/bone interface with a non-uniform pressure load, regression of the bone can occur at areas where the pressure loads are high, which could result in additional loosening of the femoral stem.

The femoral stem according to the invention has a quadrilateral cross section with edges, the cross section being in particular square, rectangular or trapezoidal. It can prove advantageous to round off these edges in order to reduce the notch effect which these edges exert on the bone cement upon sinking of the femoral stem. In addition to the notch effect, the stress peaks acting on the bone cement are of course also reduced. In an advantageous design, the edges have a radius of between 1 and 3 mm. The hip-joint prosthesis according to the invention has the further advantage that because of the quadrilateral cross section of the stem, torsional forces or shearing forces acting on the femoral stem can advantageously be transmitted to the bone cement. The quadrilateral design of the cross section of the stem and the rounding-off of the edges permit optimum functioning with respect to the two opposing requirements below:

A femoral stem with many edges leads to high stress peaks as it sinks, or even to stress fractures in the cement, so that a round cross section would be best.

On the other hand, a round cross section would generate a high shear stress in the bone cement in the event of torsional forces acting on the femoral stem, so that a cross section with corners would be more advantageous.

In a preferred embodiment, the femoral stem has a highly polished surface, as a result of which the adhesion of the cement at the cement/implant interface is reduced or avoided. The action of the shearing forces which occur along the stem as the femoral stem sinks, or also the shearing forces which occur in the cement upon torsion or bending of the stem, are additionally greatly reduced in this way.

An illustrative embodiment of the femoral hip-joint prosthesis according to the invention is explained below with reference to FIGS. 1 through 3.

BRIEF DESCRIPTION OF THE DRAWINGS

FIGS. 2a, 2b show cross sections of the stem along the line A—A and the line B—B, respectively, according to FIGS. 1 and 3, respectively, with the medullary canal and compact substance indicated;

FIGS. 6a–d show a prosthesis with three subsections, 26, 32 and 47, wherein the third subsection has a circular cross section.

DETAILED DESCRIPTION OF PREFERRED EMBODIMENTS

Figure 1:
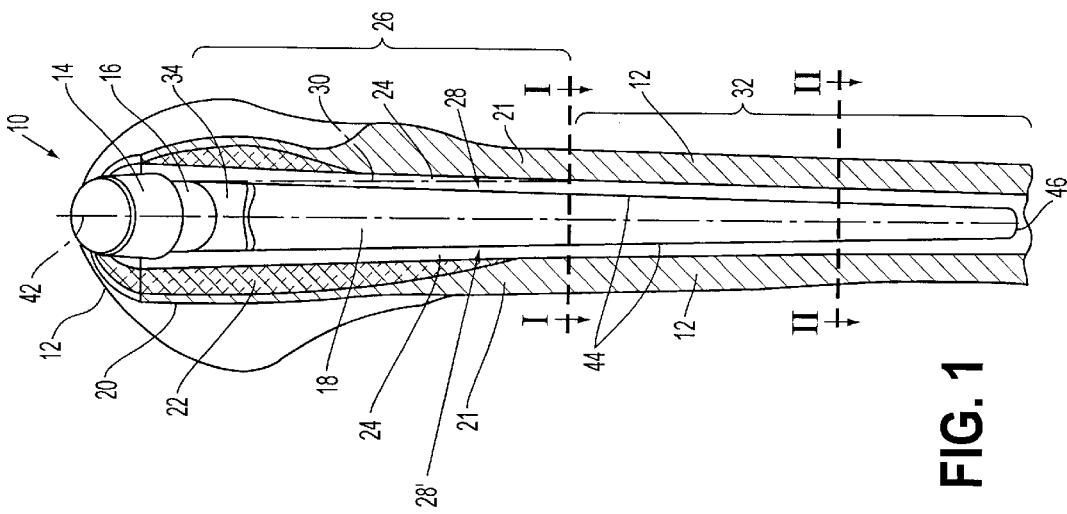
FIG. 1 shows a femoral hip-joint prosthesis from the medial direction, with the femur indicated.

FIG. 1 shows a view, from the medial direction, of a femoral hip-joint prosthesis 10 which is embedded in a femur 12 represented diagrammatically in cross section. The femoral hip-joint prosthesis 10 comprises a shoulder 34 which on one side merges seamlessly into a stem 18 and on the other side has a neck 16 which opens into a conical peg 14 on which a joint head (not shown) can be secured. The cortical substance 20, which merges into the compact substance 21, and the spongy substance 22 and medullary canal 24 are visible on the cross-sectioned femur 12. The femoral hip-joint prosthesis 10 is held in the femur 12 by means of a bone cement which fills the empty space represented in the medullary canal 24, although for the sake of improved clarity the bone cement has not been represented. In its longitudinal direction, the stem 18 has, in a first subsidiary section 26 beginning at the shoulder 34, an anterior side face and a posterior side face 28, 28', respectively, which have a curvature running logarithmically in the longitudinal direction. To clearly illustrate the curve of the side faces 28, 28', a dot-and-dash vertical line 30 has been drawn alongside the stem 18, beginning at the shoulder 34. In a second subsidiary section 32 adjoining the first subsidiary section 26, the anterior and posterior side faces 28, 28' run in a straight line, the two side faces 28, 28' converging toward the distal end.

Figure 4:
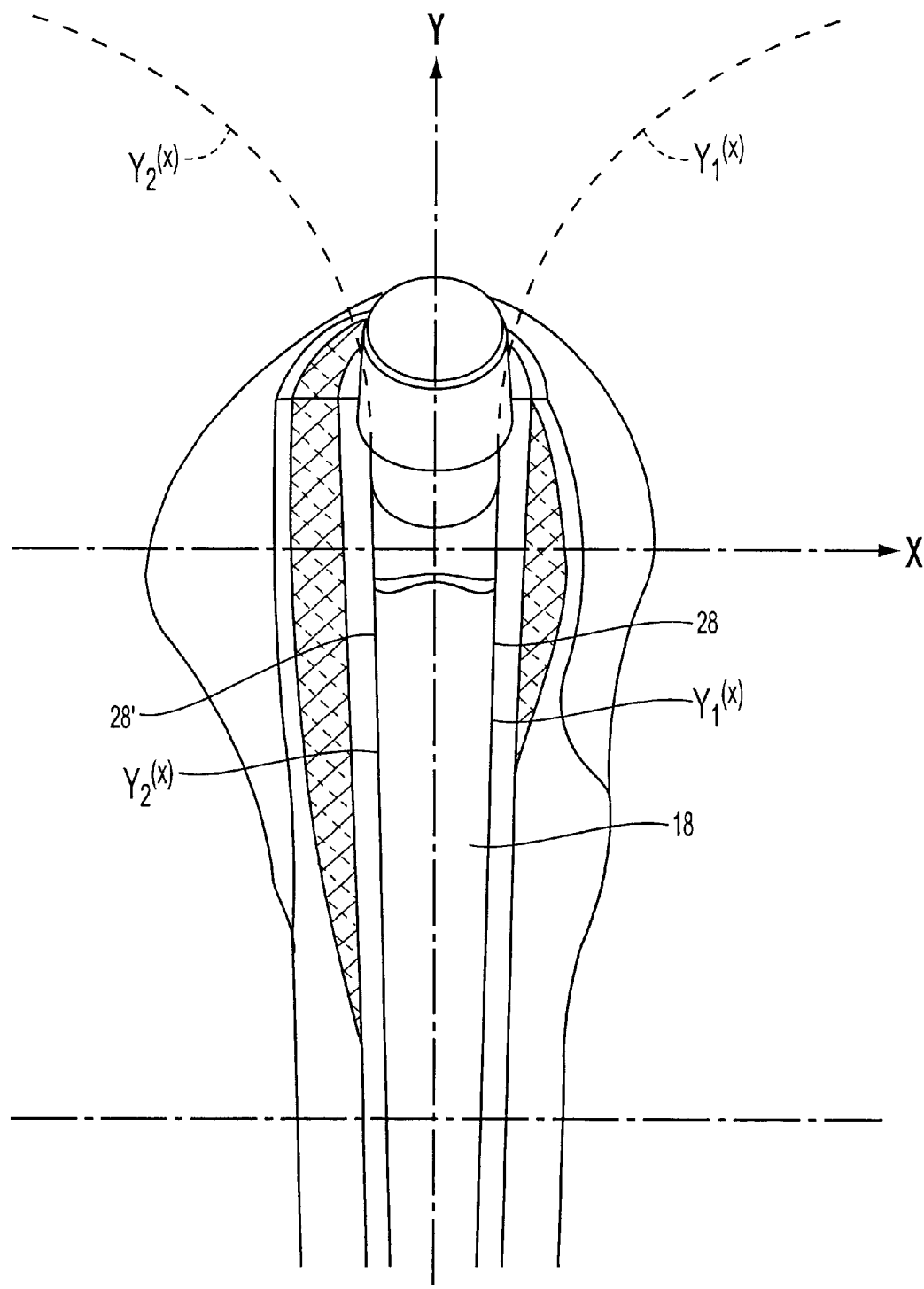
FIG. 4 shows purely schematically the extended curves $y_1(x)$ and $y_2(x)$ describing the surfaces 28 and 28', respectively.

FIG. 4 shows for clarity and purely schematically, the extended curves $y_1(x)$ and $y_2(x)$ describing the surfaces 28 and 28' respectively, in which the curvature is admittedly low.

Figure 3:
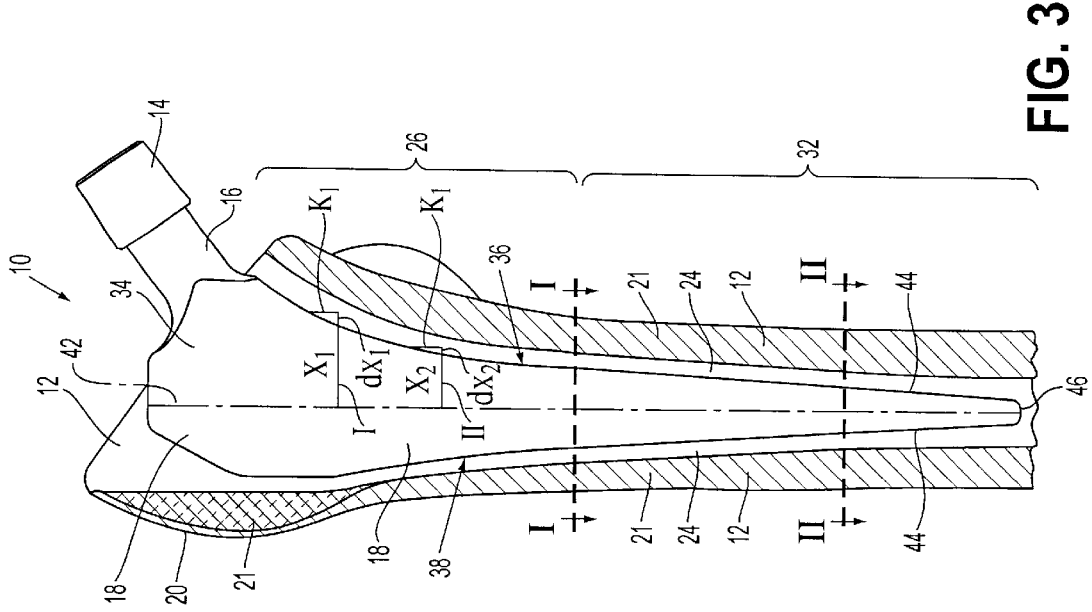
FIG. 3 shows the femoral hip-joint prosthesis from the anterior direction, with the femur indicated.

FIG. 3 shows the same femoral hip-joint prosthesis 10 according to FIG. 1 from the anterior direction. The shoulder 34 with neck 16 and peg 14 located at the proximal end of the stem 18 can clearly be seen from this perspective. In the illustrative embodiment shown, the medial side face 36 and the lateral side face 38 have, like the anterior and posterior side faces 28, 28', a first subsidiary section 26, arranged in the proximal area, with side faces 36, 38 extending in a logarithmic curve in the longitudinal direction, merging thereafter into a second subsidiary section 32 which has faces extending in a straight line. The logarithmic curvature of the medial and lateral side faces 36 and 38 begins adjoining the shoulder 34.

This configuration, according to the invention, of the side faces 28, 28' and, if appropriate, also of the side faces 36, 38, is on the one hand adapted to the natural trumpet-shaped structure in the first subsidiary section 26 and, in the second subsidiary section, to the straight-line configuration of the medullary canal 24 of the femur 12. The stem 18 is preferably fitted in the medullary canal 24 in such a way that a layer of cement with preferably an approximately constant thickness of 2 mm, for example, is obtained between the stem 18 and the femur. The function and effect of the logarithmic curvature of the side faces 28, 28' and, if appropriate, of the side faces 36, 38 in the first subsidiary section 26 are fully explained by the mathematical explanations which follow. As has already been mentioned, the stem according to the invention is designed in such a way that after it has been implanted, further sinking into the cement-filled medullary canal is possible. As is shown in FIG. 3, the logarithmic curvature of the side faces 28, 28', 36, 38 of the stem 18 means that the change in the space which the stem 18 additionally takes up as it sinks into the cement-filled medullary canal 24 remains constant or approximately constant in the direction of extension of the stem, so that the pressure also exerted approximately perpendicular to the cement/bone interface of the femur 12 is uniformly distributed in the longitudinal direction, and, as a result of this, no area with an excessively high pressure value occurs at the cement/bone interface.

Figure 5:
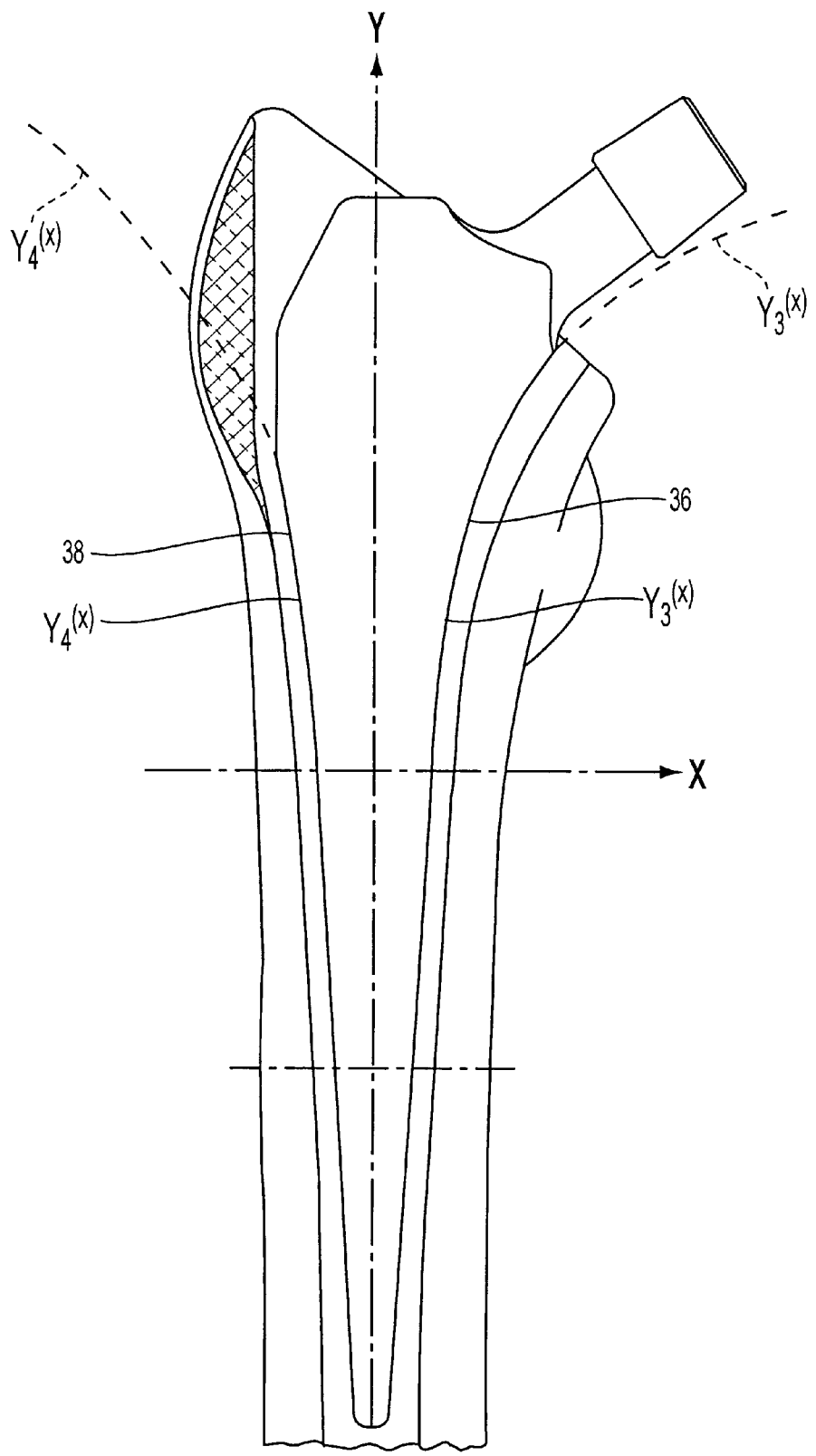
FIG. 5 shows purely schematically the extended curves $y_3(x)$ and $y_4(x)$ describing the surfaces 36 and 38, respectively.

For clarity, and purely schematically, FIG. 5 shows the extended curves $y_3(x)$ and $y_4(x)$ describing the surfaces 36 and 38, respectively, which are determined, consistent with that shown in FIG. 3, according to:

$$y(x)=K \ln|x| \qquad \text{Equation 1}$$

where K is a constant, $y(x)$ describes the curvature of the lateral surface, y denotes the direction along the longitudinal axis (or a direction parallel thereto) and x a direction perpendicular thereto. Of course, in the extended curves shown, not the whole logarithmic curve of $x \to \infty$ is shown. Rather, only a segment of each curve is shown to describe the corresponding surfaces 28, 28', 36 and 38 as appropriate.

The effect of a stem 18 sinking easily into the medullary canal 24 is explained below with reference to the example of the side face 36, although these statements do of course also apply to the side faces 28, 28' and 38, if they are designed with a logarithmically extending curve. The distance taken up by the stem 18 in the original position, on a horizontal I from a center line 42 of the stem 18 up to, for example, the medial side face 36, is given by $x_1$. The distance taken up by the stem 18 in the original position, on a horizontal II, is given by $x_2$. If the stem 18 now sinks by a constant displacement path $K_1$ in the femur 12, then the distances taken up by the stem 18 on the horizontals I and II change by $dx_1$ and $dx_2$, respectively. A concept, according to the invention, of the stem shown is that on each horizontal i the relationship of the change in the distances $dx_1$ to the original distance $x_1$ taken up by the stem 18 does not change, so that the relationship of these two distances to one another is constant, or equal to a constant $K_2$:

$$\epsilon(x_1) = \frac{dx_1}{x_1} = K_2 \quad \text{Equation 2}$$

The sinking of the stem 18 thus effects, at each horizontal i, a constant expansion $\epsilon$ which effects, perpendicular to the direction of extension of the stem, a constant expansion of the bone cement and thereby a constant increase in the pressure force in the bone cement.

Thus, on each horizontal i, the distance $dx_1$ additionally taken up after the sinking of the stem 18 is given as:

$$dx_i = x_i K_2 \quad \text{Equation 3}$$

The gradient y' of the equation $y=f(x_1)$ describing the curvature of the side face 36 at the point of the horizontal i is defined by the gradient of the tangent at this point, which is calculated as follows from the quotient of the constant displacement path $K_1$ and the distance $dx_i$ additionally taken up:

$$y'(x_i) = \tan(dx_i) = \frac{K_1}{dx_i} \quad \text{Equation 4}$$

with equation 2 gives:

$$y'(x_i) = \frac{K_1}{K_2} \cdot \frac{1}{x_i} \quad \text{Equation 5}$$

The following general curve equation is obtained for the course of the side faces 28, 28' 36, 38, where the y direction runs parallel to the center line 42:

$$y(x) = K \ln|x| \quad \text{Equation 6}$$

A side face 28, 28', 36, 38 extending as a function of the logarithm thus has the property that the space additionally taken up through the sinking of the stem 18 in the cement-filled medullary canal 24 effects a constant expansion 6 of the bone cement, which results, in the direction of extension of the stem 18, in an approximately uniform increase in the pressure transmitted from the stem 18 to the bone via the cement, or a uniform pressure distribution.

FIG. 2a shows a cross section of the stem 18 along the section line A—A, which also forms the transition between the first and second subsidiary sections 26, 32. The stem 18 is embedded in the cement-filled medullary canal 24, the cement at the cement/bone interface being surrounded by the compact substance 21. At the section line A—A shown, the stem 18 has a rectangular cross section 40. Toward the distal end of the stem 18, the cross section 40 of the stem 18 changes in such a way that, as can be seen from FIG. 2b in a section along the section line B—B, the cross section 40 has a square shape. The stem 18 is again embedded in the cement-filled medullary canal 24 and surrounded by the compact substance 21. Both illustrated cross sections of the stem 18 have edges with rounded corners 44. Along its entire length shown in FIGS. 1 and 3, the stem 18 has, for example, rounded edges 44, of which the radius is preferably between 1 and 3 mm.

The cross section of the stem 18 could also be designed in another quadrilateral shape, for example as a trapezoid or a parallelogram. Either this same cross-sectional shape extends over the entire length of the stem 18, or the different cross-sectional shapes merge one into another. A stem 18 with a cross section of such a rectangular design also preferably has rounded edges 44, the edges 44 of the stem 18 and the corners 44 of the cross section 40 preferably having a radius of between 1 and 3 mm. At the distal end 46 (FIGS. 1, 3 and 6a–d), the stem 18 can also have a circular cross section, which is essentially a third subsidiary section of the stem 18, since at this point there is usually no transmission of torsional and shearing forces.

Figure 7A:
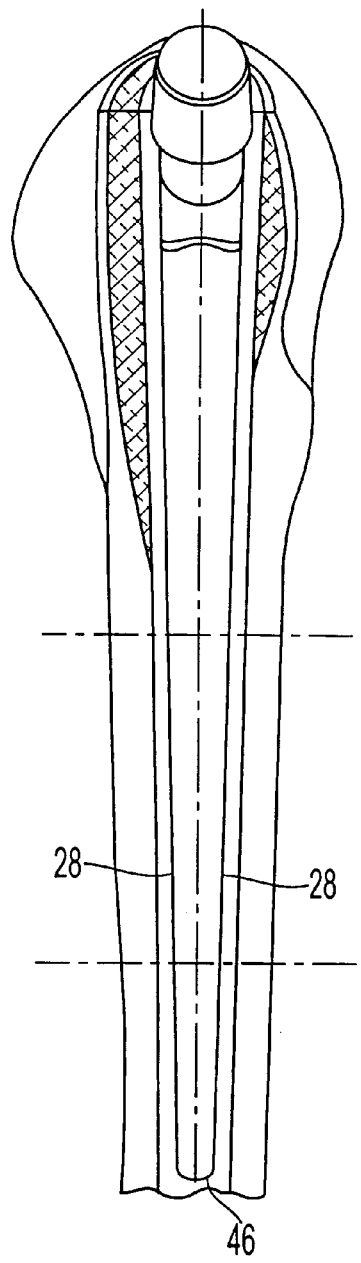
FIGS. 7a, 7b show a prosthesis with parallel faces near the distal end.
Figure 7B:
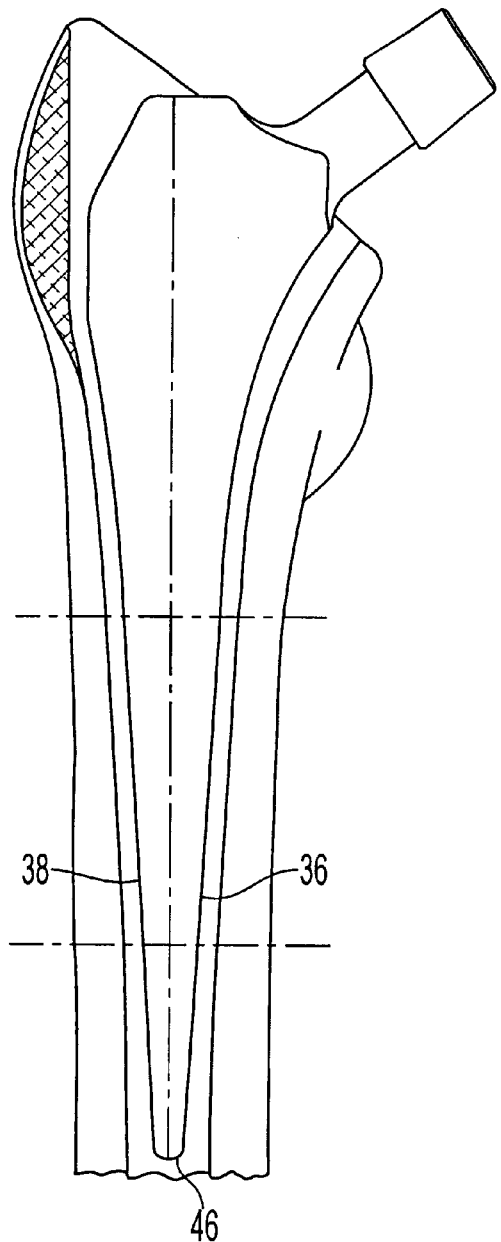

Starting from the distal end 46, the side faces 28, 28' and 36, 38 of the stem 18 extend parallel to one another along a length of up to 5 mm as seen, for example, in FIGS. 7a and 7b. This end section, which is essentially a third subsidiary section of the stem 18, can be used for receiving a centering sleeve which allows the distal end 46 to be centered in the medullary canal 24.

In the illustrative embodiment shown, the point of transition from the logarithmically curved side faces 28, 28' and 36, 38 of the first subsidiary section 26 to the rectilinearly converging side faces 28, 28' and 36, 38 of the second subsidiary section 32 is arranged at the level of the section line A—A. This point of transition can also be located, for example, in relation to the longitudinal direction, in the central area of the stem 18, but preferably approximately in the lower third of the stem 18, so that the second subsidiary section 32, starting from the distal end 46, extends along half, preferably a third, of the stem 18.

The femoral stem 18 is made, for example, of a biocompatible metal such as titanium, or a titanium alloy or a CoCrMo alloy having highly polished surfaces.

What is claimed is:

1. A femoral hip-joint prosthesis for implantation by cement with a stem having a longitudinal axis, a proximal end, a distal end, a collarless shoulder, an anterior side face and a posterior side face, a first subsidiary section and a second subsidiary section, wherein the collarless shoulder is located in the region of said proximal end;

the stem has in at least one portion a quadrilateral cross section;

the stem extends along the longitudinal axis and tapers from the proximal end toward the distal end;

the first subsidiary section begins in the region of the proximal end and extends along the longitudinal axis;

the second subsidiary section is located distally of the first subsidiary section and extends along the longitudinal axis; and the anterior side face and the posterior side face, in the direction of the longitudinal axis, have, in the first subsidiary section, a logarithmically extending curvature and thereafter, in the second subsidiary section, extend in a straight line and converge.

2. The femoral hip-joint prosthesis as claimed in claim 1, wherein the stem has medial and lateral side faces, the medial and lateral side faces each having, in the direction of extension of the stem, in a first subsidiary section beginning at the shoulder, a logarithmically extending curvature, and thereafter, in a second subsidiary section, extending in a straight line and converging.

3. The femoral hip-joint prosthesis as claimed in claim 1, wherein the second subsidiary section, starting from the distal end, extends along up to half of the stem.

4. The femoral hip-joint prosthesis as claimed in claim 1, wherein the quadrilateral cross section forms edges which are rounded.

5. The femoral hip-joint prosthesis as claimed in claim 4, wherein the rounded edges have a radius of between 1 and 3 mm.

6. The femoral hip-joint prosthesis as claimed in claim 1, wherein the quadrilateral cross section is selected from the group consisting of the trapezoidal, rectangular and square shapes, the cross section, from the proximal end to the distal end of the stem, being able to merge from one into another of these shapes.

7. The femoral hip-joint prosthesis as claimed in claim 1, wherein the stem has a third subsidiary section in the distal end section with a circular cross section.

8. The femoral hip-joint prosthesis as claimed in claim 1, wherein the side faces, starting from the distal end, extend to one another along a length of up to 5 mm.

9. The femoral hip-joint prosthesis as claimed in claim 1, wherein at least the side faces of the stem have a highly polished surface.

10. The femoral hip-joint prosthesis as claimed in claim 1, wherein the second subsidiary section, starting from the distal end, extends along a third subsidiary section of the stem.

* * * * *